(12) United States Patent
Atsumi

(10) Patent No.: US 11,940,781 B2
(45) Date of Patent: Mar. 26, 2024

(54) SEWING MANAGEMENT SYSTEM AND SEWING MANAGEMENT METHOD

(71) Applicant: JUKI CORPORATION, Tama (JP)

(72) Inventor: Tadashi Atsumi, Tokyo (JP)

(73) Assignee: JUKI CORPORATION, Tama (JP)

( * ) Notice: Subject to any disclaimer, the term of this patent is extended or adjusted under 35 U.S.C. 154(b) by 503 days.

(21) Appl. No.: 17/159,473

(22) Filed: Jan. 27, 2021

(65) Prior Publication Data

US 2021/0232127 A1    Jul. 29, 2021

(30) Foreign Application Priority Data

Jan. 28, 2020   (JP) ................. 2020-011534

(51) Int. Cl.
| | |
|---|---|
| G05B 19/418 | (2006.01) |
| D05B 19/04 | (2006.01) |
| G06Q 10/0631 | (2023.01) |
| G06Q 10/0639 | (2023.01) |

(52) U.S. Cl.
CPC ....... *G05B 19/41875* (2013.01); *D05B 19/04* (2013.01); *G06Q 10/063112* (2013.01); *G06Q 10/06398* (2013.01); *G05B 2219/45195* (2013.01)

(58) Field of Classification Search
CPC .............................................. G05B 19/41875
See application file for complete search history.

(56) References Cited

U.S. PATENT DOCUMENTS

| | | | |
|---|---|---|---|
| 2001/0004717 A1* | 6/2001 | Zhang ............... | D05C 5/00 |
| | | | 700/136 |
| 2009/0066521 A1* | 3/2009 | Atlas ................ | A61B 5/18 |
| | | | 340/575 |
| 2015/0265201 A1 | 9/2015 | Arbas | |

(Continued)

FOREIGN PATENT DOCUMENTS

| | | | |
|---|---|---|---|
| CN | 101363167 A | * | 2/2009 |
| DE | A1-102016215250 | | 2/2018 |

(Continued)

OTHER PUBLICATIONS

Extended European Search Report dated Jun. 15, 2021 in corresponding European patent application No. 21153905.1 (7 pages).

(Continued)

*Primary Examiner* — Suresh Suryawanshi
(74) *Attorney, Agent, or Firm* — Faegre Drinker Biddle & Reath LLP

(57) ABSTRACT

The sewing management system includes a sewing machine that performs sewing on a sewing line, a management server that manages various information on the sewing line, and a wearable terminal that detects physical condition management information of an operator on the sewing line. The sewing machine transmits production management information, including identification information of the operator who perform sewing operations on the sewing line and operation information of the main unit of the device, to the management server. The management server estimates a sewing skill of the operator based on the production management information and estimates the production capacity of the operator based on the physical condition management information.

10 Claims, 9 Drawing Sheets

(56) References Cited

U.S. PATENT DOCUMENTS

| | | | |
|---|---|---|---|
| 2019/0003094 A1* | 1/2019 | Fujimoto | G05B 19/182 |
| 2019/0233995 A1* | 8/2019 | Atsumi | D05B 19/08 |
| 2019/0370722 A1* | 12/2019 | Serita | H04W 4/38 |
| 2020/0311645 A1* | 10/2020 | Atsumi | G06Q 10/06393 |
| 2021/0125518 A1* | 4/2021 | Wada | G06Q 10/06398 |
| 2021/0287155 A1* | 9/2021 | Kotake | A61B 5/165 |

FOREIGN PATENT DOCUMENTS

| | | |
|---|---|---|
| JP | A-H08-107989 | 4/1996 |
| JP | A-H09-131478 | 5/1997 |
| JP | 2001-276453 A | 10/2001 |
| JP | 2014-153847 A | 8/2014 |
| JP | A-2016-214511 | 12/2016 |
| JP | 2017-173899 A | 9/2017 |
| JP | 2018-055493 A | 4/2018 |
| JP | 2019-197466 A | 11/2019 |
| KR | 101995275 B1 | 7/2019 |

OTHER PUBLICATIONS

Japanese Office Action dated Nov. 14, 2023 in Application No. 2020-011534.

* cited by examiner

FIG.6

| No. | ITEM ID | PROCESS ID | OPERATOR ID | SEWING MACHINE ID | STANDARD DATA | | | OPERATION DATA | | | NUMBER OF DEFECTS | ERROR | POSITIONAL INFORMATION | COMPLETION DATE AND TIME |
|---|---|---|---|---|---|---|---|---|---|---|---|---|---|---|
| | | | | | STANDARD PARAMETER 1 STANDARD SEWING TIME | STANDARD PARAMETER 2 STANDARD SEWING SPEED | | OPERATION DATA 1 SEWING TIME | OPERATION DATA 2 SEWING SPEED | VOLUME | | | | |
| 1 | TP01 | ST1 | OP1 | M01 | TS2 | NS2 | | TS3 | NS3 | 100 | 0 | 0 | ... | 2018/12/3 11:15 |
| 2 | TP01 | ST1 | OP2 | M02 | TS2 | NS2 | | TS3 | NS3 | 80 | 0 | 0 | N1,E1 | 2018/12/3 11:30 |
| 3 | TP01 | ST1 | OP3 | M03 | TS2 | NS2 | | TS1 | NS1 | 60 | 3 | 10 | ... | 2018/12/3 11:45 |
| 4 | TP01 | ST2 | OP1 | M04 | TS2 | NS2 | | TS3 | NS3 | 100 | 0 | 0 | ... | 2018/12/3 13:15 |
| 5 | TP01 | ST2 | OP2 | M05 | TS2 | NS2 | | TS2 | NS2 | 80 | 5 | 0 | S1,W1 | 2018/12/3 13:30 |
| 6 | TP01 | ST2 | OP3 | M06 | TS2 | NS2 | | TS1 | NS1 | 60 | 0 | 20 | N2,W2 | 2018/12/3 13:45 |
| 7 | TP01 | ST3 | OP1 | M07 | TS2 | NS2 | | TS3 | NS3 | 100 | 0 | 0 | ... | 2018/12/3 14:15 |
| 8 | TP01 | ST3 | OP2 | M08 | TS2 | NS2 | | TS1 | NS1 | 70 | 0 | 0 | ... | 2018/12/3 14:30 |
| 9 | TP01 | ST3 | OP3 | M09 | TS2 | NS2 | | TS1 | NS1 | 60 | 5 | 15 | ... | 2018/12/3 14:45 |
| 10 | TP02 | ST4 | OP1 | M10 | TS2 | NS2 | | | | | | | | |
| | TP02 | ST4 | OP2 | M11 | TS2 | NS2 | | | | | | | | |
| | TP02 | ST4 | OP3 | M12 | TS2 | NS2 | | | | | | | | |
| | TP03 | ST5 | OP1 | M13 | TS2 | NS2 | | | | | | | | |
| | TP03 | ST5 | OP2 | M14 | TS2 | NS2 | | | | | | | | |
| | TP03 | ST5 | OP3 | M15 | TS2 | NS2 | | | | | | | | |

| No. | OPERATOR ID | MEASUREMENT DATE AND TIME | DAY OF WEEK | DETERMINATION ELEMENT ||||||| STATUS |
| --- | --- | --- | --- | --- | --- | --- | --- | --- | --- | --- |
| | | | | TEMPER-ATURE | HEART RATE | BLOOD PRESSURE | NUMBER OF STEPS | WORKING HOURS | NUMBER OF BREAKS | |
| 1 | OP1 | 2019/6/10 9:00 | MON | 36.5 | 60 | 70-100 | 0 | 0 | 0 | S |
| 2 | OP1 | 2019/6/10 13:00 | MON | 36.6 | 65 | 75-110 | 300 | 3 | 1 | S |
| 3 | OP1 | 2019/6/10 15:00 | MON | 36.5 | 60 | 70-100 | 500 | 5 | 1 | S |
| 4 | OP1 | 2019/6/10 17:00 | MON | 37.0 | 60 | 70-100 | 700 | 7 | 2 | A |
| 5 | OP1 | 2019/6/11 9:00 | TUE | 36.5 | 60 | 70-100 | 0 | 0 | 0 | S |
| 6 | OP1 | 2019/6/11 13:00 | TUE | 36.6 | 65 | 75-110 | 300 | 3 | 1 | S |
| 7 | OP1 | 2019/6/11 15:00 | TUE | 36.5 | 60 | 70-100 | 500 | 5 | 1 | S |
| 8 | OP1 | 2019/6/11 17:00 | TUE | 37.0 | 60 | 70-100 | 700 | 7 | 2 | A |
| 9 | OP1 | 2019/6/12 9:00 | WED | 36.5 | 60 | 70-100 | 0 | 0 | 0 | S |
| 10 | OP1 | 2019/6/12 13:00 | WED | 36.6 | 65 | 75-110 | 300 | 3 | 1 | S |
| 11 | OP1 | 2019/6/12 15:00 | WED | 36.5 | 60 | 70-100 | 500 | 5 | 1 | S |
| 12 | OP1 | 2019/6/12 17:00 | WED | 37.0 | 60 | 70-100 | 700 | 7 | 2 | A |
| 13 | OP1 | 2019/6/12 19:00 | WED | 37.0 | 70 | 75-115 | 900 | 9 | 3 | B |
| 14 | OP1 | 2019/6/12 21:00 | WED | 37.2 | 70 | 75-115 | 1100 | 11 | 3 | B |
| 15 | OP1 | 2019/6/13 13:00 | THU | 37.5 | 70 | 75-115 | 0 | 0 | 0 | C |
| 16 | OP1 | 2019/6/13 13:00 | THU | 37.5 | 70 | 75-115 | 300 | 3 | 1 | C |
| 17 | OP1 | 2019/6/13 15:00 | THU | 37.5 | 70 | 75-115 | 500 | 5 | 1 | C |
| 18 | OP1 | 2019/6/13 17:00 | THU | 37.7 | 70 | 75-115 | 700 | 7 | 2 | D |
| 19 | OP1 | 2019/6/14 9:00 | FRI | 37.0 | 70 | 75-115 | 0 | 0 | 0 | B |
| 20 | OP1 | 2019/6/14 13:00 | FRI | 37.0 | 70 | 70-100 | 300 | 3 | 1 | B |
| 21 | OP1 | 2019/6/14 15:00 | FRI | 37.0 | 70 | 70-100 | 500 | 5 | 1 | B |
| 22 | OP1 | 2019/6/14 17:00 | FRI | 37.0 | 90 | 70-100 | 700 | 7 | 2 | D |

1100

| No. | OPERATOR ID | PROCESS ID | SKILL |
|---|---|---|---|
| 1 | OP1 | ST1 | 100 |
| 2 | OP1 | ST2 | ... |
| 3 | OP1 | ST3 | ... |
| 4 | OP2 | ST1 | 80 |
| 5 | OP2 | ST2 | ... |
| 6 | OP2 | ST3 | ... |
| 7 | OP3 | ST1 | 57 |
| 8 | OP3 | ST2 | ... |
| 9 | OP3 | ST3 | ... |

SEWING MANAGEMENT SYSTEM AND SEWING MANAGEMENT METHOD

CROSS-REFERENCE TO RELATED APPLICATIONS

The present application claims the benefit of priority of Japanese Patent Application No. 2020-011534, filed on Jan. 28, 2020, the content of which is incorporated herein by reference.

TECHNICAL FIELD

The present invention relates to a sewing management system and a sewing management method.

BACKGROUND ART

A sewing management system is known that can easily and reliably select a series of sewing procedures or sewing data at the time of sewing, and additionally, can easily collect production management data such as sewing history data during sewing work (for example, refer to Japanese Unexamined Patent Application Publication No. 2001-276453). The sewing management system includes a detachable recording medium including a first storage region for storing sewing schedule information, a second storage region for storing sewing data, and a third storage region for storing production management information. Accordingly, the production management information during the sewing work can be accumulated in the recording medium for each sewing work or for each sewing machine, and thus, it is possible to improve productivity of production management in the sewing work.

However, in the above-described sewing management system, the production management information accumulated in the recording medium does not include operator-related information including the sewing skill and the physical condition information of the operator who performs the sewing work. Therefore, it is not expected to improve the sewing quality and the production efficiency in the sewing line after taking into account the sewing skill and the physical condition information of the operator. In a sewing factory, it is required to improve the sewing quality and the production efficiency in the sewing line after taking into account the sewing skill and the physical condition information of the operator.

SUMMARY OF INVENTION

In such view, one of the objects of the present invention is to provide a sewing management system and a sewing management method capable of improving the sewing quality and the production efficiency in a sewing line.

According to an aspect of the present invention, there is provided a sewing management system comprises a sewing device that transmits production management information including identification information of an operator and operation information of a device main body, a terminal that detects physical condition management information of the operator, and a management device that manages the production management information for each process of a product sewn in a sewing line or for each process of a component that configures the product, and manages the physical condition management information for each operator, wherein the management device estimates a sewing skill of the operator based on the production management information and estimates production capacity of the operator based on the physical condition management information.

According to another aspect of the present invention, there is provided a sewing management method using a sewing device that performs sewing in a sewing line, a management device that manages each piece of information in the sewing line, and a terminal that detects physical condition management information of an operator of the sewing line, the method comprises a step of transmitting production management information including identification information of the operator and operation information of the sewing device, from the sewing device, a step of transmitting the physical condition management information of the operator from the terminal, a step of managing the production management information for each process of a product sewn in the sewing line or for each process of a component that configures the product, by the management device, a step of managing the physical condition management information for each operator, by the management device, a step of estimating a sewing skill of the operator based on the production management information, by the management device, and a step of estimating production capacity of the operator based on the sewing skill and the physical condition management information of the operator, by the management device.

According to the sewing management system and the sewing management method according to one aspect of the present invention, the production management information including the identification information of the operator and the operation information of the sewing device is managed for each process of a product sewn in a sewing line or for each process of a component that configures the product, and the physical condition management information is managed for each operator. The sewing skill of the operator is estimated based on the production management information, and the production capacity of the operator is estimated based on the physical condition management information. Accordingly, by setting the personnel assignment and the like in the sewing line, it is possible to improve the sewing quality and the production efficiency in the sewing line.

BRIEF DESCRIPTION OF DRAWINGS

FIG. 6 is an explanatory view of an example of a production management information table held in a table holding unit of the management server;

FIG. 7 is an explanatory view of an example of a physical condition management information table held in the table holding unit of the management server;

DESCRIPTION OF EMBODIMENTS

Figure 1:
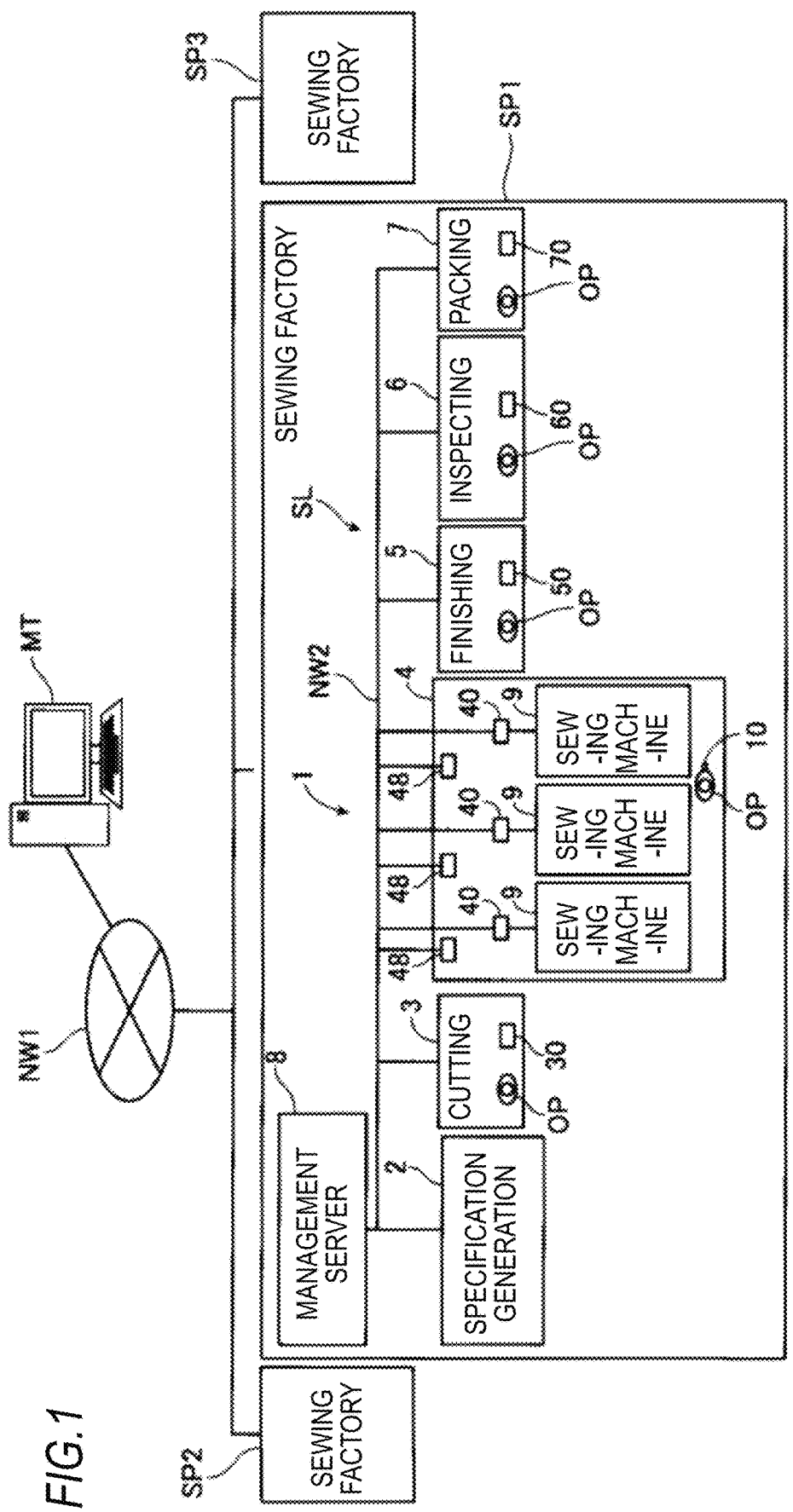
FIG. 1 is a network configuration view of a sewing management system according to a present embodiment.

Hereinafter, a sewing management system will be described with reference to the attached drawings. FIG. 1 is a network configuration view of a sewing management system 1 according to the embodiment. As illustrated in FIG. 1, the sewing management system 1 is applied to a sewing line SL constructed in sewing factories SP (SP1 to SP3) to improve the sewing quality and the production efficiency in the sewing line SL. In FIG. 1, the details of the sewing line SL are illustrated only for the sewing factory SP1, and will be omitted for the sewing factories SP2 and SP3.

The sewing factories SP (SP1 to SP3) illustrated in FIG. 1 are connected to a network NW1 such as the Internet. Persons involved in the sewing factory SP (for example, employees of the company that owns the sewing factory SP or those who supply equipment to the sewing factory SP) can confirm the operating situation or the like of the sewing factory SP from a management terminal MT. For example, the management terminal MT can confirm the operating situation or the like of the sewing factory SP by acquiring the information managed by a management server 8 in the sewing factory SP (will be described later). It is also possible to change the settings of various parameters in the sewing line SL from the management terminal MT. The management terminal MT is configured with a general personal computer (PC), a tablet PC, a smart device (smartphone, smart watch, or smart glasses) and the like.

The sewing line SL includes a plurality of processes for producing a single or a plurality of sewn products (hereinafter, simply referred to as "products"). The sewing line SL illustrated in FIG. 1 includes a specification generation process 2, a cutting process 3, a sewing process 4, a finishing process 5, an inspecting process 6, and a packing process 7. The process of configuring the sewing line SL is not limited to the example illustrated in FIG. 1, and can be changed as appropriate. Here, the line including a plurality of processes illustrated in FIG. 1 is called the sewing line SL, but the name is not limited thereto, and can be changed as appropriate. In the following description, an object in the process of producing a product is appropriately referred to as a sewn material.

In the execution region of various processes included in the sewing line SL, the equipment necessary for executing the corresponding work process is installed. In the sewing management system 1 according to the embodiment, the pieces of equipment are directly or indirectly connected to each other via a network (for example, LAN or WAN) NW2 constructed in the sewing factory SP. The management server 8 as a management device that manages the entire system is connected to the network NW2. As will be described in detail later, the management server 8 manages various pieces of information output from the equipment of each process or the wearable terminal that the operator of each process wears, the sewing skill and the production capacity of the operator in the sewing line SL are estimated based on the managed information, and further, the sewing quality and the production efficiency in the sewing line SL are analyzed. Hereinafter, the contents of each process included in the sewing line SL and the equipment to be installed will be described.

The specification generation process 2 is a process of generating the specifications of the product to be sewn in the sewing line SL, and setting sewing data for sewing the product according to the generated specifications, and parameters (hereinafter, referred to as "setting parameters") and standard time which are set for various pieces of equipment required for packing the product. For example, in the execution region of the specification generation process 2, a personal computer (PC) equipped with applications such as a computer-aided design (CAD) or computer-aided manufacturing (CAM) is provided as equipment. The PC is connected to the network NW2 of the sewing management system 1. The PC in the specification generation process 2 outputs the specifications, the sewing data, the setting parameters, the standard time, and the like to the management server 8.

The cutting process 3 is a process of cutting the cloth based on the specifications or CAD/CAM data. For example, in the execution region of the cutting process 3, a stretching machine, a releasing/shrinking machine, a cutting machine, a mobile terminal 30 connected to the cutting machine in a wired or wireless manner, and the like, are provided as equipment. The mobile terminal 30 is connected to the network NW2 of the sewing management system 1. In the cutting process 3, the cloth wound in a roll shape is released by a releasing/shrinking machine, and is cut by the cutting machine in a state where the distortion or wrinkle of the cloth is removed. Identification information is given to the cloth after cutting, and for example, an RFID tag is attached to the cloth. An item number ID indicating the identification information of the product or component is recorded in the RFID tag. The mobile terminal 30 connected to the cutting machine outputs information such as the item number ID read by the terminal main body and the number of cutting sheets output from the cutting machine, to the management server 8.

The sewing process 4 is a process of sewing the cloth cut in the cutting process 3 based on the specifications, the sewing data, the setting parameters, and the like. In the execution region of the sewing process 4, a sewing machine 9 as a single or a plurality of sewing devices, a mobile terminal 40 connected to the sewing machine 9 in a wired or wireless manner, a conveying device of the sewn material, and the like, are provided. The mobile terminal 40 is connected to the network NW2 of the sewing management system 1. The mobile terminal 40 outputs information such as operation data, error data, and volume data of the sewing machine 9 connected to the mobile terminal 40, to the management server 8. The mobile terminal 40 outputs the identification information such as the item number ID or the operator ID read by the mobile terminal 40, to the management server 8.

At a predetermined position in the execution region of the sewing process 4, a position detecting device 48 for detecting the positional information of the operator is installed. The position detecting device 48 reads, for example, the operator ID in the ID card carried by the operator in a non-contact manner. The position detecting device 48 is configured to be able to detect the position of the operator at any position within the detectable region. The position detecting device 48 is connected to the network NW2 of the sewing management system 1. The position detecting device 48 outputs the detected positional information of the operator to the management server 8 via the network NW2. As the position detection method by the position detecting device 48, any method such as RFID, beacon, GPS or image recognition can be adopted.

The finishing process 5 is a process of performing final finishing before the inspecting process such as iron pressing, buttoning, and thread cutting with respect to the sewn material sewn in the sewing process 4 based on the specifications. In the execution region of the finishing process 5, an iron press machine and the like, a mobile terminal 50 connected to the iron press machine and the like in a wired or wireless manner, are provided. The mobile terminal 50 is connected to the network NW2 of the sewing management system 1. The mobile terminal 50 connected to the iron press machine or the like outputs information such as volume data output from the iron press machine or the like to the management server 8, in addition to the item number ID or the operator ID read by the terminal main body.

The inspecting process 6 is a process of inspecting the sewn material finally finished in the finishing process 5 based on the specifications. In the execution region of inspecting process 6, an inspection table, an inspection machine, an inspection meter, a mobile terminal 60 connected to these, and the like, are provided. The mobile terminal 60 is connected to the network NW2 of the sewing management system 1. The inspection machine is configured such that the inspector can input the inspection result of the sewn material and the number of inspected sewn materials. The mobile terminal 60 connected to the inspection machine or the like outputs information such as inspection results, volume data, and defect data which are output from the inspection machine to the management server 8, in addition to the item number ID or the operator ID read by the terminal main body.

The packing process 7 is a process of packing the sewn material inspected in the inspecting process 6 based on the specifications. In the execution region of the packing process 7, a tagging machine, a mobile terminal 70 connected to the tagging machine and the like in a wired or wireless manner, are provided. The mobile terminal 70 is connected to the network NW2 of the sewing management system 1. The mobile terminal 70 connected to the tagging machine outputs information such as volume data and completion date/time which are output from the tagging machine to the management server 8, in addition to the item number ID or the operator ID read by the terminal main body.

In the execution regions of various processes included in the sewing line SL, an operator OP who executes the corresponding work process is assigned. The operator OP has a terminal 10 configured to be detachably attached to the body. The terminal 10 configures an example of the terminal that detects the physical condition management information of the operator OP who works in the sewing line SL. For example, the terminal 10 is configured with a wearable terminal, but is not limited thereto. Hereinafter, the terminal 10 will be described as a wearable terminal 10. FIG. 1 illustrates a case where the wearable terminal 10 is attached only to the operator OP in the sewing process 4, but the wearable terminal 10 can also be attached to the operator OP assigned to various processes other than the sewing process 4.

The wearable terminal 10 is configured to be attached to the wrist or the like of the operator OP and to be able to detect the biological information of the operator OP. For example, the wearable terminal 10 can detect the body temperature, heart rate, blood pressure, and the like of the operator OP as biological information, but is not limited thereto, and can detect any biological information. The wearable terminal 10 is configured to be able to detect the activity amount of the operator OP. For example, the wearable terminal 10 can detect the number of steps of the operator OP as activity amount, but is not limited thereto, and can detect any activity amount. These biological information and activity amount information configure an example of physical condition management information of the operator OP.

The sewing management system 1 according to the embodiment includes the management server 8, some or all pieces of equipment of various processes, and some or all of the wearable terminals 10 that the operators OP of various processes wear. For example, the sewing management system 1 includes, as an example of the equipment, the sewing machine 9 and the position detecting device 48 in the sewing process 4, and the mobile terminals 30, 40, 50, 60, and 70 and the wearable terminal 10 in various processes. However, the configuration of the sewing management system 1 is not limited thereto, and can be changed as appropriate.

Figure 2:
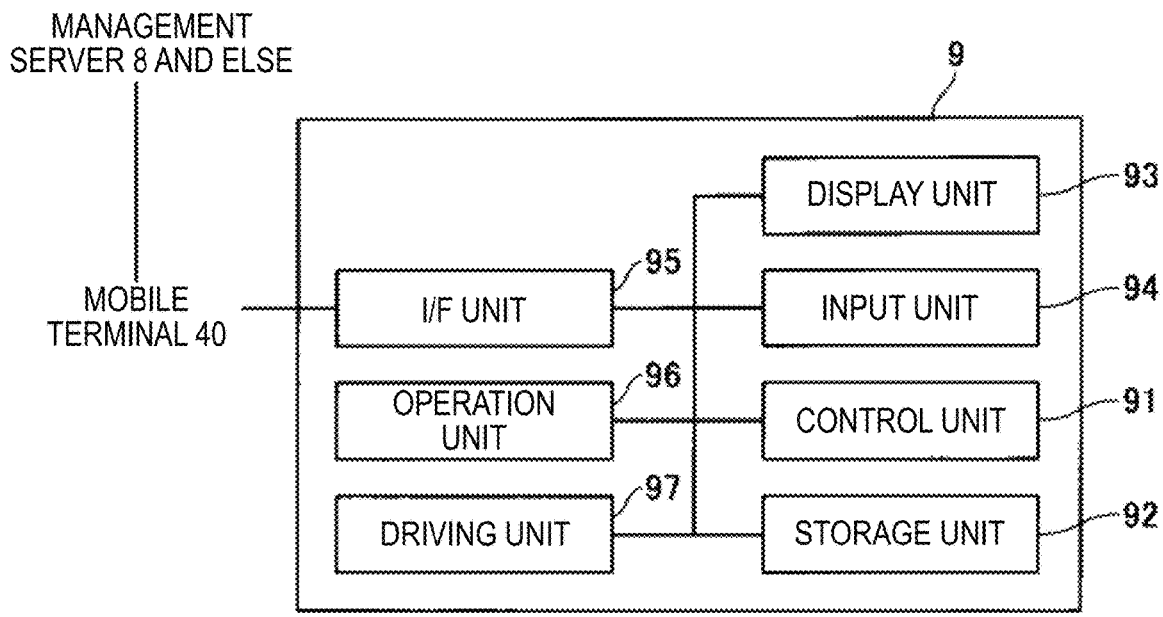
FIG. 2 is a block diagram illustrating a configuration of a sewing machine included in the sewing management system.
Figure 3:
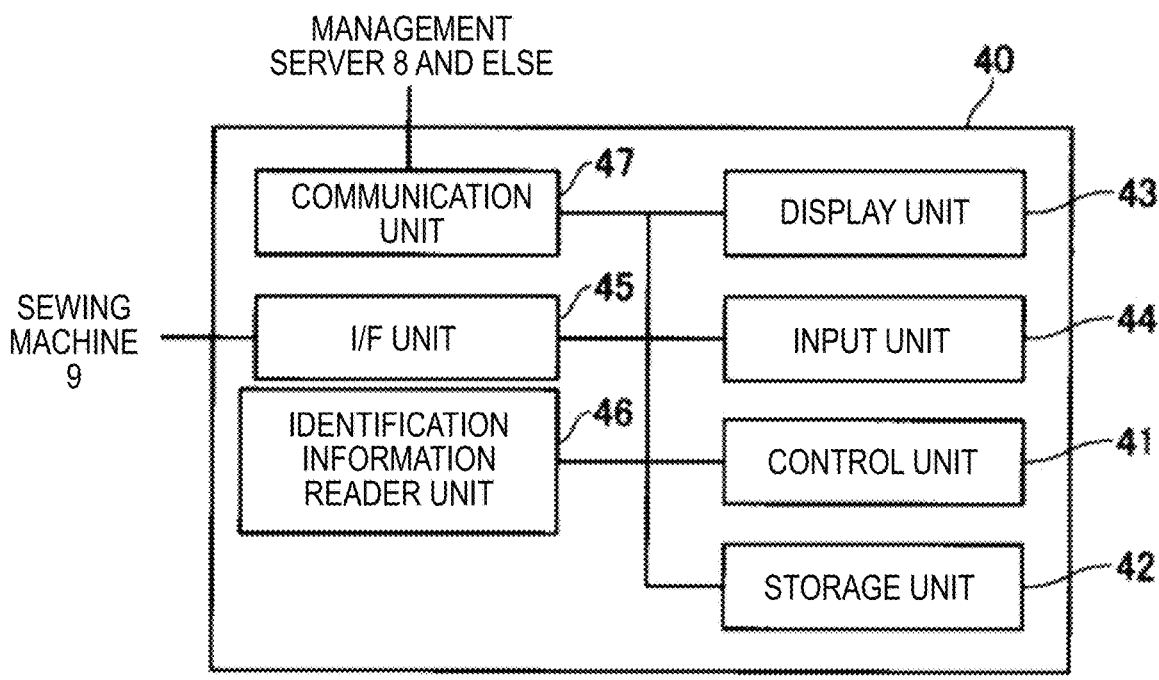
FIG. 3 is a block diagram illustrating a configuration of a mobile terminal included in the sewing management system.
Figure 4:
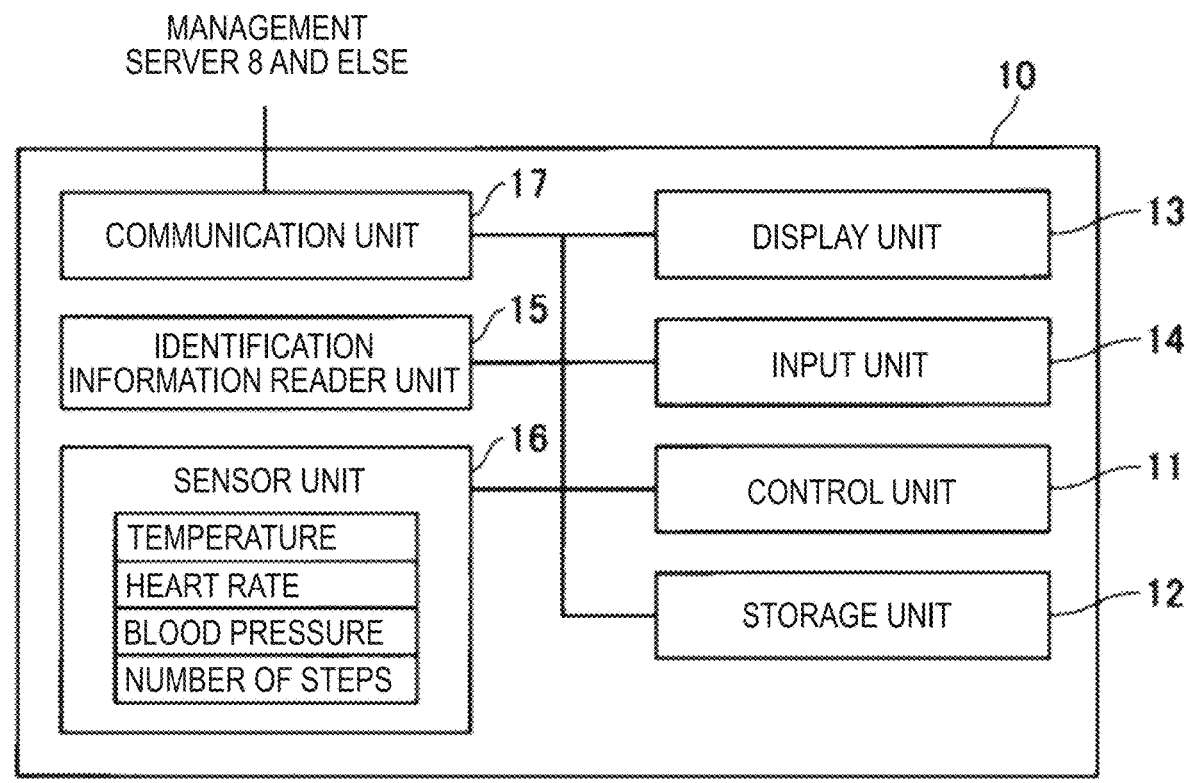
FIG. 4 is a block diagram illustrating a configuration of a wearable terminal included in the sewing management system.

Here, the configurations of the sewing machine 9, the mobile terminals 30, 40, 50, 60, and 70, and the wearable terminal 10 that configure the sewing management system 1 according to the embodiment will be described with reference to FIGS. 2, 3, and 4. Since the mobile terminals 30, 40, 50, 60, and 70 basically have a common configuration, the mobile terminal 40 will be described as a representative example. FIG. 2 is a block diagram illustrating a configuration of the sewing machine 9 included in the sewing management system 1 according to the embodiment. FIG. 3 is a block diagram illustrating a configuration of the mobile terminal 40 included in the sewing management system 1 according to the embodiment. FIG. 4 is a block diagram illustrating a configuration of the wearable terminal 10 included in the sewing management system 1 according to the embodiment.

As illustrated in FIG. 2, the sewing machine 9 includes a control unit 91 that controls the entire sewing machine 9, and a storage unit 92, a display unit 93, an input unit 94, an interface unit (I/F unit) 95, an operation unit 96, and a driving unit 97 which are connected to the control unit 91. The control unit 91 is configured with a central processing unit such as a CPU. The storage unit 92 stores the program executed by the control unit 91 and functions as a work region of the control unit 91.

The display unit 93 displays information necessary for the operation of the sewing machine 9. For example, the display unit 93 displays an operation screen for operating the sewing machine 9, an item number ID of the sewn material, a setting parameter for the sewn material, and the like. The input unit 94 receives an input of an instruction from the operator. For example, the input unit 94 receives an input of a setting parameter change instruction for the sewing machine 9 from the operator. In FIG. 2, the display unit 93 and the input unit 94 have separate configurations, but the invention is not limited thereto. For example, a touch panel or the like may have the functions of the display unit 93 and the input unit 94.

The I/F unit 95 configures an interface between the external terminal and the control unit 91. The mobile terminal 40 is connected to the I/F unit 95. Information are exchanged between the sewing machine 9 and the mobile terminal 40 via the I/F unit 95. For example, operation data or volume data of the sewing machine 9 are output to the mobile terminal 40.

The operation unit 96 receives the driving operation from the operator. For example, the operation unit 96 receives the hand movement driving operation (for example, a hand movement start/end operation, a hand movement direction instruction operation, and the like) from the operator. The driving unit 97 drives the sewing machine needle or the like according to the driving operation from the operator.

With such a configuration, the sewing machine 9 performs sewing according to the instruction of the operator from the operation unit 96. The driving at the time of sewing is performed according to the setting parameters set in the specification generation process 2. For example, sewing is performed according to the feeding rate or the hand movement speed of the sewn material set as setting parameters. The setting parameters in the sewing machine 9 can be changed from the input unit 94 according to the sewing skill of the operator. The setting parameters changed by the operator are output to the management server 8 via the mobile terminal 40. The operation information of the driving unit 97 according to the preset setting parameter (or the changed setting parameter) is output to the management server 8 via the mobile terminal 40.

As illustrated in FIG. 3, the mobile terminal 40 includes a control unit 41 that controls the entire terminal, and a storage unit 42, a display unit 43, an input unit 44, an interface unit (I/F unit) 45, an identification information reader unit 46, and a communication unit 47 which are connected to the control unit 41. The control unit 41 is configured with a central processing unit such as a CPU. The storage unit 42 stores the program executed by the control unit 41 and functions as a work region of the control unit 41.

The display unit 43 displays information necessary for the operation of the mobile terminal 40. For example, the display unit 43 displays an operation screen for operating the mobile terminal 40, an item number ID and an operator ID read by the identification information reader unit 46 (will be described later), and the like. The input unit 44 receives an input of an operation instruction from the operator. For example, the input unit 44 receives an instruction to read the operator ID or the item number ID from the operator. In FIG. 3, the display unit 43 and the input unit 44 have separate configurations, but the invention is not limited thereto. For example, a touch panel or the like may have the functions of the display unit 43 and the input unit 34.

The I/F unit 45 configures an interface between the external terminal and the control unit 41. The sewing machine 9 is connected to the I/F unit 45. Information are exchanged between the cutting machine and the mobile terminal 40 via the I/F unit 45. For example, the operation information in the driving unit 97 of the sewing machine 9 or the volume data in the sewing machine 9 are output to the mobile terminal 40. The identification information reader unit 46 reads the operator ID in the ID card carried by the operator, the item number ID in the RFID tag attached to the cloth, or the like in a non-contact manner. The communication unit 47 communicates with the management server 8 and the like via the network NW2 of the sewing management system 1. For example, the communication unit 47 transmits the operator ID or the item number ID read via the identification information reader unit 46, the operation information of the sewing machine 9 received via the I/F unit 45, or the like, to the management server 8.

With such a configuration, the mobile terminal 40 receives the operation information and the like of the sewing machine 9 via the I/F unit 45. The mobile terminal 40 reads the operator ID in the ID card carried by the operator, the item number ID in the RFID tag attached to the cloth, or the like, according to the instruction from the input unit 44. The number of cut sheets and the operator ID or the item number ID are output to the management server 8 via the communication unit 47.

The mobile terminals 30, 50, 60, and 70 of the cutting process 3, the finishing process 5, the inspecting process 6, and the packing process 7 have different objects to be connected via the I/F unit, and information to communicate with the connection objects is different. A cutting machine is connected to the mobile terminal 30, and the number of sheets cut by the cutting machine is output. An iron press machine is connected to the mobile terminal 50 to receive volume data and the like. An inspection machine or the like is connected to the mobile terminal 60 to receive inspection results, volume data, defect data, and the like. The tagging machine is connected to the mobile terminal 70 to receive volume data, completion date/time, and the like.

As illustrated in FIG. 4, the wearable terminal 10 includes a control unit 11 that controls the entire terminal, and a storage unit 12, a display unit 13, an input unit 14, an identification information reader unit 15, a sensor unit 16, and a communication unit 17 which are connected to the control unit 11. The control unit 11 is configured with a central processing unit such as a CPU. The storage unit 12 stores the program executed by the control unit 11 and functions as a work region of the control unit 11.

The display unit 13 displays information necessary for the operation of the wearable terminal 10. For example, the display unit 13 displays an operation screen for operating the wearable terminal 10, an operator ID read by the identification information reader unit 15 (will be described later), and the like. The input unit 14 receives an input of an operation instruction from the operator OP. For example, the input unit 14 receives an instruction to read the operator ID from the operator OP. In FIG. 4, the display unit 13 and the input unit 14 have separate configurations, but the invention is not limited thereto. For example, a touch panel or the like may have the functions of the display unit 13 and the input unit 14.

The identification information reader unit 15 reads the operator ID and the like in the ID card carried by the operator OP in a non-contact manner. The sensor unit 16 detects the biological information and the activity amount information of the operator OP who is wearing the terminal. Here, it is assumed that the sensor unit 16 can detect the body temperature, heart rate, and blood pressure of the operator OP as biological information, and can detect the number of steps of the operator OP as activity amount information. The communication unit 17 communicates with the management server 8 and the like via the network NW2 of the sewing management system 1. For example, the communication unit 17 transmits the operator ID read via the identification information reader unit 15 and the biological information or the activity amount information of the operator OP detected by the sensor unit 16, to the management server 8.

With such a configuration, the wearable terminal 10 reads the operator ID in the ID card carried by the operator by the identification information reader unit 15 according to an instruction from the input unit 14. The wearable terminal 10 detects the biological information and the activity amount information of the operator OP by the sensor unit 16 according to the instruction from the input unit 14 or at a predetermined time. The operator ID, the biological information, and the like are output to the management server 8 via the communication unit 17.

The management server 8 manages the information output from the equipment in various processes. The pieces of information are used as information for managing the production in the sewing line SL. In the following, for convenience of description, these pieces of information will be referred to as "production management information". The management server 8 manages the pieces of production management information for each product sewn in the sewing line SL or for each component that configures the product. The management server 8 manages the information output from the wearable terminal 10. The pieces of information are used as information for managing the physical condition of the operator (physical condition management information). The management server 8 manages the physical condition management information for each operator. The management server 8 estimates the sewing skill of the operator based on the production management information, and estimate the production capacity of the operator based on the physical condition management information. The management server 8 analyzes the sewing quality and the production efficiency in the sewing line SL according to these estimation results. The production management information and the physical condition management information managed by the management server 8 will be described later.

Figure 5:
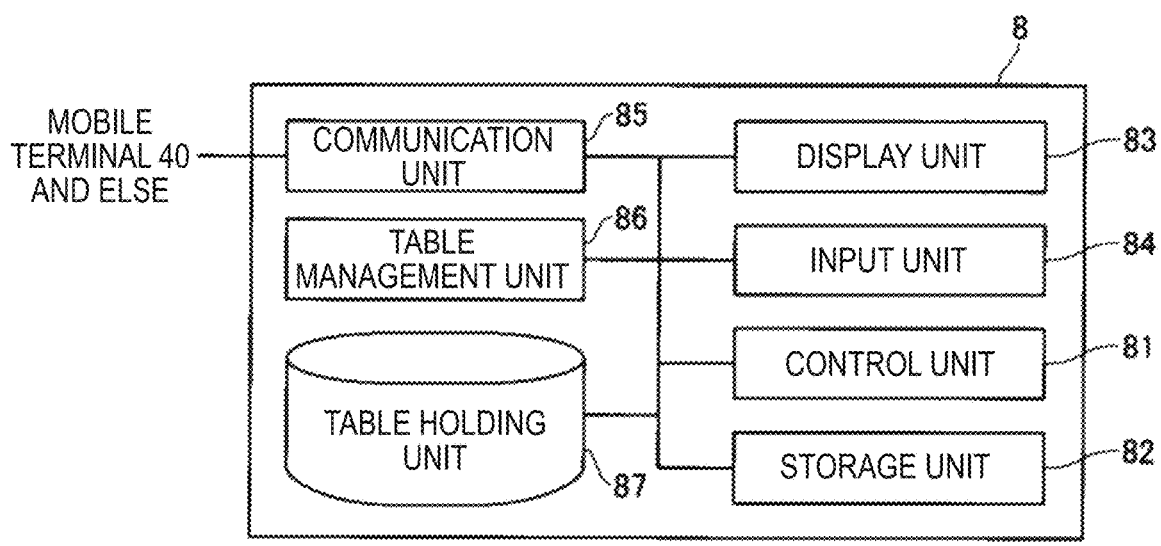
FIG. 5 is a block diagram illustrating a configuration of a management server included in the sewing management system.

FIG. 5 is a block diagram illustrating a configuration of the management server 8 that configures the sewing management system 1 according to the embodiment. As illustrated in FIG. 5, the management server 8 includes a control unit 81 that controls the entire server, and a storage unit 82, a display unit 83, an input unit 84, a communication unit 85, a table management unit 86, and a table holding unit 87 which are connected to the control unit 81. The control unit 81 is configured with a central processing unit such as a CPU. The storage unit 82 stores the program executed by the control unit 81 and functions as a work region of the control unit 81.

The display unit 83 displays information necessary for the operation of the management server 8. For example, the display unit 83 displays an operation screen for operating the management server 8, an analysis result screen for displaying the analysis result of the sewing line SL based on the production management information, and the like. The input unit 84 receives an input such as an operation instruction from the administrator of the management server 8. For example, the input unit 84 receives an analysis instruction of the sewing line SL from the administrator. In FIG. 5, the display unit 83 and the input unit 84 have separate configurations, but the invention is not limited thereto. For example, a touch panel or the like may have the functions of the display unit 83 and the input unit 84.

The communication unit 85 communicates with the equipment of various processes of the sewing line SL via the network NW2 of the sewing management system 1. For example, the communication unit 85 receives the production management information including the operator ID or the operation information in the driving unit 97 from the mobile terminal 40 in the sewing process 4. The communication unit 85 communicates with the wearable terminal 10 of various processes of the sewing line SL via the network NW2 of the sewing management system 1. For example, the communication unit 85 receives the physical condition management information including the operator ID or the biological information from the wearable terminal 10 in the sewing process 4.

The table management unit 86 generates a production management information table from the production management information received by the communication unit 85, and manages the production management information. The table management unit 86 generates a physical condition management information table from the physical condition management information received by the communication unit 85, and manages the physical condition management information. The table holding unit 87 holds the production management information table and the physical condition management information table generated by the table management unit 86. The table holding unit 87 holds a sewing skill table (will be described later).

Here, an example of the production management information table and the physical condition management information table held in the table holding unit 87 will be described with reference to FIGS. 6 and 7. FIG. 6 is an explanatory view of an example of a production management information table 600 held in the table holding unit 87 of the management server 8 according to the embodiment. FIG. 7 is an explanatory view of an example of a physical condition management information table 700 held in the table holding unit 87 of the management server 8 according to the embodiment. The registered contents of the production management information table 600 and the physical condition management information table 700 held in the table holding unit 87 are not limited to the contents illustrated in FIGS. 6 and 7, and can be changed as appropriate.

In the production management information table 600 illustrated in FIG. 6, the production management information regarding the item number ID (TP01 to TP03) associated with one component of a T-shirt which is a product is registered. For example, the item number IDs "TP01", "TP02", and "TP03" are associated with sewing work corresponding to the "body part", "sleeve", and "collar" of the T-shirt which is a product, respectively. The item number ID "TP01" is associated with the work of sewing the front body part and the rear body part. The item number ID "TP02" and "TP03" are associated with the work of sewing sleeves and a collar to the front and rear body parts, respectively. The contents of the item number IDs are determined based on the information from the PC in the specification generation process 2, and are registered based on the information from the mobile terminal 30 in the cutting process 3.

In the production management information table 600, as standard data, the standard sewing time is registered as a standard parameter 1 (parameter 1), and the standard sewing speed is registered as a standard parameter 2 (parameter 2). It is assumed that the standard parameter 1 is set to "TS3" indicating a fast sewing time, "TS1" indicating a slow sewing time, and "TS2" indicating an intermediate sewing time. It is assumed that the standard parameter 2 is set to "NS3" indicating a high sewing speed, "NS1" indicating a low sewing speed, and "NS2" indicating an intermediate sewing time. The contents of the standard parameters 1 and 2 are registered based on the information from the PC in the specification generation process 2.

In the production management information table 600, for the item number ID "TP01", "TP02", and "TP03", the production management information in a case where three different operators perform sewing work using three different sewing machines 9, is registered. The operator IDs (OP1 to OP3) are associated with each of the three operators. Sewing machine IDs (M01 to M03) are associated with each of the three sewing machines 9. The operator IDs and sewing machine IDs are preset by the administrator of the sewing management system 1 and the like, and are registered based on the information from the sewing machine 9 in the sewing process 4.

In the production management information table 600, the actual sewing time in the sewing machine 9 is registered as operation data 1, and the actual sewing speed in the sewing machine 9 is registered as operation data 2. The contents registered in the operation data 1 and 2 are the same as the standard parameters 1 and 2, respectively. In other words, "TS1", "TS2", or "TS3" is registered as the sewing time, and "NS1", "NS2", or "NS3" is registered as the sewing speed. The contents of the operation data 1 and 2 are registered based on the information from the sewing machine 9 in the sewing process 4.

The positional information of the operator of the sewing machine 9 is registered in the production management information table 600. The contents registered in the positional information are, for example, how far apart in the north, south, east, and west directions is registered with reference to the position of the position detecting device 48 installed in the sewing process 4. For example, in the production management information of number #2, "N1: E1" is registered. The information indicates that the operator has moved to a position separated from the position of the position detecting device 48 by one block in the north direction and by one block in the east direction. Here, the "block" is a unit of a predetermined distance. Similarly, in the production management information of number #6, it is registered as "N2: W2". The information indicates that the operator has moved to a position separated from the position of the position detecting device 48 by two blocks in the north direction and by two blocks in the west direction. The contents of the pieces of positional information are registered based on the information from the position detecting device 48 of the sewing process 4. Regarding the position detection method of the operator, movement may be detected (estimated) by a position detection sensor such as GPS provided in the wearable terminal.

In the production management information table 600, the volume data of the product (sewn material), the inspection result (number of defects) data, the defect (error) data, and the completion date/time data are registered. The number of the products that has been sewn by the sewing machine 9 is registered in the volume data, and the inspection result of the product is registered in the inspection result data. In the former, the actual number of products is registered, and in the latter, for example, the defective rate (or non-defective rate) is registered. The number of occurrences of defects in the sewing machine 9 is registered in the defect data, and the date and time when the packing work is completed is registered in the completion date/time data. In the former, the number of actual occurrences of defects of the sewing machine 9 (for example, a feed error of the sewn material or a hand movement error) is registered. The volume data is registered based on the information from the sewing machine 9 in the sewing process 4. The contents of the inspection result data and the defect data are registered based on the information from the mobile terminal 60 in the inspecting process 6. The contents of the completion date/time data are registered based on the information from the mobile terminal 70 in the packing process 7.

In the production management information table 600 illustrated in FIG. 6, as illustrated in numbers #1 to #3, it can be known that, for the item number ID "TP01", three different operators (operators OP1 to OP3) perform the sewing work of the same process (ST1) using three different sewing machines 9 (M01 to M03). It can be known that, while the sewing time (TS2) and the sewing speed (NS2) are set by the standard parameters 1 and 2, the operators OP1 and OP2 are actually working at the sewing time of TS3 and at the sewing speed of NS3. Meanwhile, it can be known that, while the sewing time (TS2) and the sewing speed (NS2) are set by the standard parameters 1 and 2, the operator OP3 is actually working at the sewing time of TS1 and the sewing speed of NS1. Therefore, the sewing time and the sewing speed differ depending on the operator.

It can be known that, while the operators OP1 and OP3 did not move from the reference position (installation position of the position detecting device 48), the operator OP2 moved to the northeast side by one block from the reference position. It can be known that the volume data of the products of the operators OP1, OP2, and OP3 are 100, 80, and 60, respectively. It can be known that, while the inspection result of the products of the operators OP1 and OP2 is the number of defects "0", the inspection result of the product of OP3 is the number of defects "3". It can be known that, while defects did not occur in the sewing machine 9 of M01 and M02, defects occurred 10 times in the sewing machine 9 of M03. It can be known that the product completion time by the operator OP1 is the earliest (11:15 on Dec. 3, 2018), and the product completion time by the operators OP2 and OP3 continues in this order (11:30 and 11:45 on the same day, respectively).

Here, an aspect of registering the production management information in such a production management information table 600 will be described with reference to FIGS. 1, 5, and 6. For example, in the sewing process 4, when the operator reads the item number ID and the operator ID with the identification information reader unit of the mobile terminal 40, the pieces of information are output to the management server 8 as production management information and recorded in the storage unit 82. Here, the sewing machine ID of the sewing machine 9 connected to the mobile terminal 40 is also output to the management server 8 and recorded in the storage unit 82. Information such as sewing data and standard parameters output from the specification generation process 2 are also recorded in the storage unit 82. When the item number ID, the process ID, the operator ID, and the sewing machine ID are recorded in the storage unit 82, and the table management unit 86 calls the standard parameters 1 and 2 based on the item number ID, and registers the information in the production management information table 600. Accordingly, the item number ID, the standard parameter 1, the standard parameter 2, the operator ID, and the sewing machine ID are registered in the production management information table 600.

When the actual sewing work is performed in the sewing process 4, the operation data and the volume data associated with the sewing work are output to the management server 8 and recorded in the storage unit 82. The positional information of the operator is output from the position detecting device 48 in the sewing process 4 to the management server 8 and recorded in the storage unit 82. When the information are recorded in the storage unit 82, the table management unit 86 registers the operation data, the volume data, and the positional information of the operator in the production management information table 600. Accordingly, the operation data 1, the operation data 2, the positional information of the operator, and the volume data are registered in the production management information table 600.

When the product (sewn material) is inspected in the inspecting process 6, the product inspection result data and the defect data in the sewing machine 9 are output from the mobile terminal 60 to the management server 8 and recorded in the storage unit 82. When the data are recorded in the storage unit 82, the table management unit 86 registers the inspection result data and the defect data in the production management information table 600. Accordingly, the inspection result data and the defect data are registered in the production management information table 600.

When the sewn material is packed in the packing process 7, the completion date/time data is output from the mobile terminal 70 to the management server 8 and recorded in the storage unit 82. When the completion date/time data is recorded in the storage unit 82, the table management unit 86 registers the completion date/time data in the production management information table 600. Accordingly, the completion date/time data is registered in the production management information table 600. As such, all pieces of production management information of the production management information table 600 illustrated in FIG. 6 are registered.

In the physical condition management information table 700 illustrated in FIG. 7, the biological information (body temperature, heart rate, and blood pressure), the activity amount information (number of steps), working hours, and number of breaks of the corresponding operator are registered for each measurement date and time in association with the operator ID. In the physical condition management information table 700, the physical condition status (status) of the operator, which is determined by using these biological information, activity amount information, working hours, and the number of breaks as determination factors, is registered.

The physical condition management information table 700 illustrated in FIG. 7 illustrates a case where the physical condition management data from 9:00 on Jun. 10, 2019 to 17:00 on Jun. 14, 2019 is registered in the operator with the operator ID "OP1". In the physical condition management information table 700, the biological information and the like are measured at a predetermined fixed time. Specifically, the biological information and the like are measured at 9:00, which is the work start time in the morning of each day, at 13:00, which is the work start time in the afternoon, and every two hours after 13:00. Regarding the working hours, the elapsed time from 9 o clock is recorded. The number of breaks is recorded by counting the break at lunch, the break from 15:15 to 15:30, and the break from 17:30 to 18:00.

A plurality of ranks (ranks S, A, B, C, and D) are registered in the physical condition status by comprehensively determining the registered contents of the determination factors. The rank S indicates that the physical condition of the operator is in the best state. A state where the physical condition of the operator gradually deteriorates in the order of ranks A, B, C, and D is illustrated. The rank of the physical condition status is not limited thereto, and can be changed as appropriate.

Here, a method for determining the physical condition status will be described by taking the body temperature and the heart rate as an example. For example, in the physical condition management information table 700, in a case where the body temperature of the operator is 36.5° C. to 36.8° C., the rank S is set. The rank is lowered by one in a case where the body temperature is 36.9° C. to 37.2° C., the rank is lowered by two in a case where the body temperature is 37.3° C. to 37.6° C., and the rank is lowered by three in a case where the body temperature is 37.7° C. or higher. In a case where the heart rate of the operator is 60 to 69 times, the rank S is set. It is determined that the rank is lowered by one in a case where the heart rate is 70 to 79 times, the rank is lowered by two in a case where the heart rate is 80 to 89 times, and the rank is lowered by three in a case where the heart rate is 90 times or more. In the physical condition management information table 700, the rank of the physical condition status is set by comprehensively determining these factors.

For example, in the physical condition management information table 700, in the physical condition management data of #4, since the body temperature is 37.0° C. and the heart rate is 60 times, the rank is lowered by one with respect to the body temperature, and the physical condition status becomes the rank A. According to the physical condition management data of #13, since the body temperature is 37.0° C. and the heart rate is 70 times, the rank is lowered by one with respect to the body temperature and the rank is lowered by one with respect to the heart rate, and the physical condition status becomes the rank B.

Similarly, according to the physical condition management data of #17, since the body temperature is 37.5° C. and the heart rate is 70 times, the rank is lowered by two with respect to the body temperature and the rank is lowered by one with respect to the heart rate, and the physical condition status becomes the rank C. According to the physical condition management data of #18, since the body temperature is 37.7° C. and the heart rate is 70 times, the rank is lowered by three with respect to the body temperature and the rank is lowered by one with respect to the heart rate, and the physical condition status becomes the rank D. According to the physical condition management data of #22, since the body temperature is 37.0° C. and the heart rate is 90 times, the rank is lowered by one with respect to the body temperature and the rank is lowered by three with respect to the heart rate, and the physical condition status becomes the rank D.

Here, for convenience of description, a case where only the body temperature and the heart rate are referred to in the method for determining the physical condition status will be described. Other determination factors are also associated with the method for determining the actual physical condition status. For example, by determining the physical condition status according to the level of blood pressure of the operator, the length of working hours, and the number of breaks acquired, the physical condition status according to the physical condition of the operator can be managed on the physical condition management information table 700.

Figure 8:
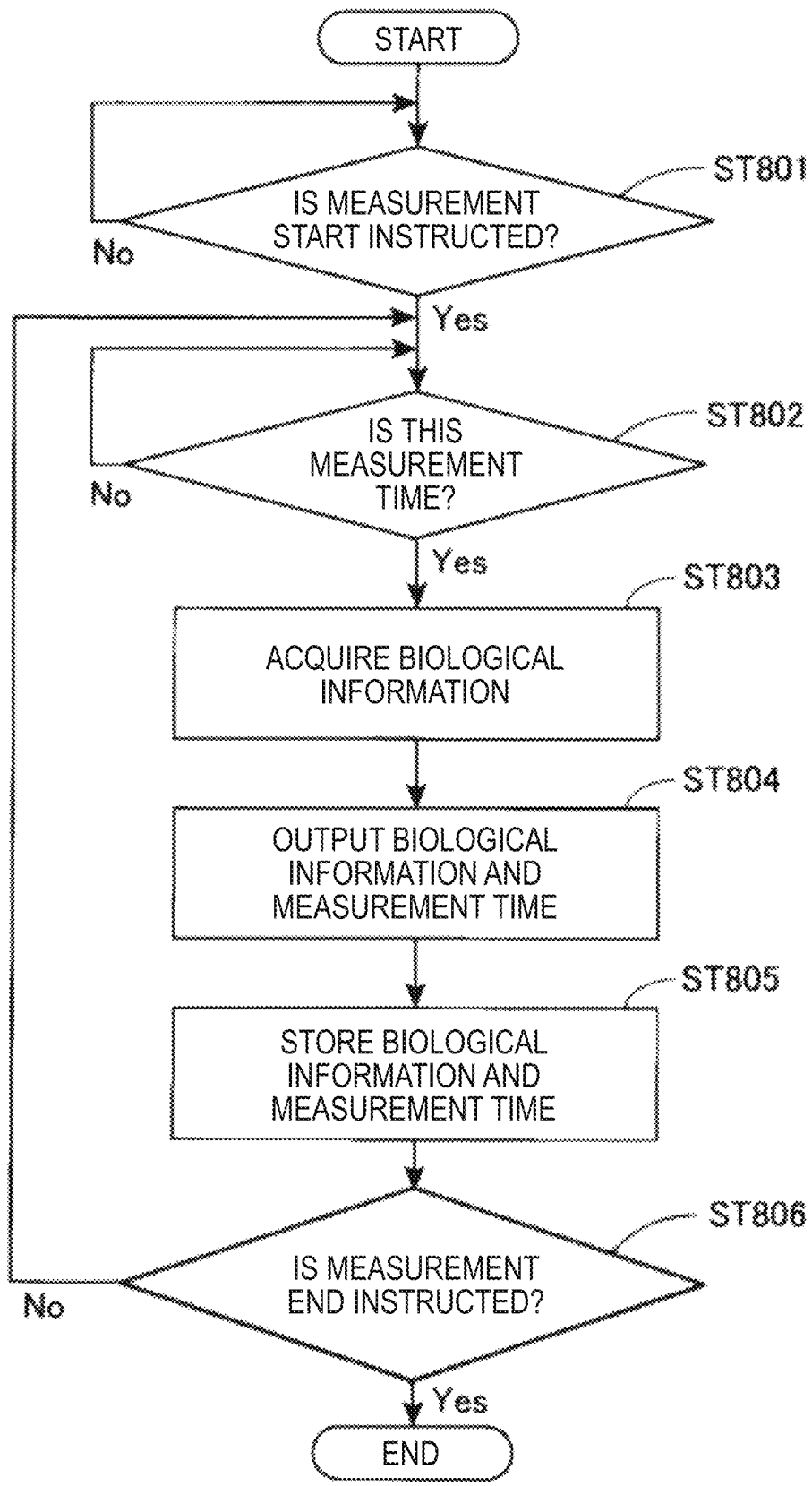
FIG. 8 is a flowchart for describing a registration process of physical condition management information for the physical condition management information table.
Figure 9:
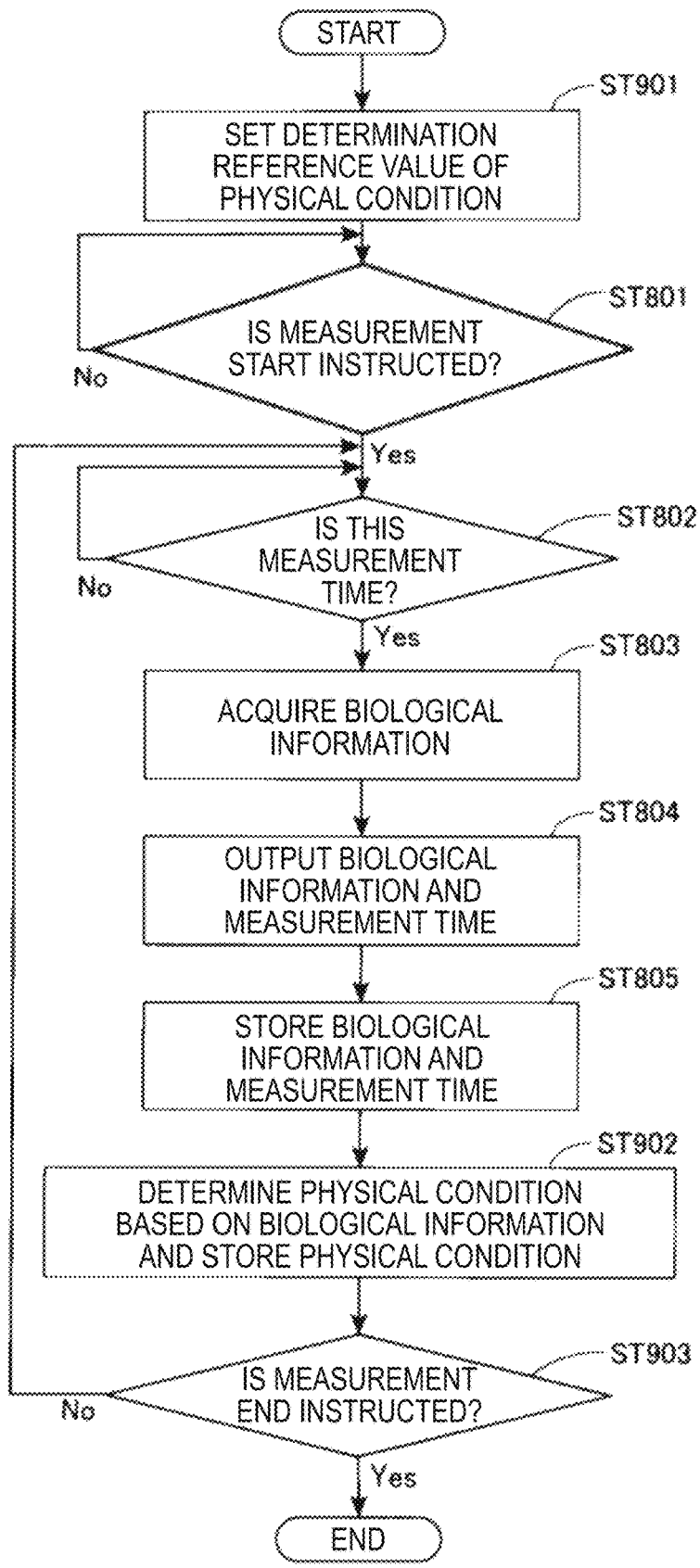
FIG. 9 is a flowchart for describing a determination process of the physical condition management information for the physical condition management information table.

Here, an aspect of registering the physical condition management data in the physical condition management information table 700 will be described with reference to FIGS. 8 and 9. FIGS. 8 and 9 are flowcharts for describing an example of the registration process of the physical condition management information for the physical condition management information table 700 in the management server 8 according to the embodiment. In FIGS. 8 and 9, for convenience of description, the process of registering the biological information as the physical condition management information will be described. Since the process of registering the activity amount information as the physical condition management information is the same as that of the biological information, the description thereof will be omitted.

FIG. 8 illustrates a process of accumulating the physical condition management information (biological information) prior to registration of physical condition management data in the physical condition management information table 700. Meanwhile, FIG. 9 illustrates a process of registering the physical condition management information including the physical condition status based on a determination reference value set from the accumulated physical condition management information. FIGS. 8 and 9 illustrate a case where the biological information is measured by the wearable terminal 10 at a predetermined measurement time.

As illustrated in FIG. 8, in the wearable terminal 10, the control unit 11 determines whether there is a measurement start instruction of the biological information (physical condition management information) of the operator (step (hereinafter, referred to as "ST") 801). For example, the control unit 11 determines whether the measurement start instruction is received from the operator via the input unit 14. The control unit 11 may determine the measurement start instruction of the biological information in a case where the operator ID is read via the identification information reader unit 15. In a case where the measurement start instruction of the biological information is not detected (ST801: No), the control unit 11 continues the determination process of ST801.

In a case where the measurement start instruction of the biological information is detected (ST801: Yes), the control unit 11 determines whether the current time has reached a predetermined measurement time (ST802). Here, it is assumed that the measurement time is set to 9:00, 13:00, and every two hours after 13:00. The control unit 11 determines the measurement time according to the time information measured by the clocking unit (not illustrated). In a case where the current time has not reached the measurement time (ST802: No), the determination process of ST802 is repeated until the measurement time is reached.

In a case where the current time has reached the measurement time (ST802: Yes), the control unit 11 instructs the sensor unit 16 to acquire the biological information. When receiving the instruction, the sensor unit 16 acquires the biological information (ST803). When the sensor unit 16 acquires the biological information, the control unit 11 outputs the biological information acquired via the communication unit 17 and the measuring time of the biological information, to the management server 8 (ST804). The management server 8 stores the biological information in the storage unit 82. When the biological information is stored in the storage unit 82, the table management unit 86 registers the stored biological information in the physical condition management information table 700 (ST805).

After outputting the biological information and the measurement time, the control unit 11 of the wearable terminal 10 determines whether there is a measurement end instruction of the biological information of the operator OP (ST806). For example, the control unit 11 determines whether the measurement end instruction is received from the operator via the input unit 14. In a case where the measurement end instruction of the biological information is not detected (ST806: No), the control unit 11 returns the process to ST802 and repeats the process after ST802. When the measurement end instruction of the biological information is detected while repeating the processes from ST802 to ST806 (ST806: Yes), the control unit 11 ends the accumulation process of a series of biological information (physical condition management data) illustrated in FIG. 8.

As such, the biological information of the operator is registered in the physical condition management information table 700. When the biological information of the operator is registered, as illustrated in FIG. 9, the administrator of the management server 8 sets the reference value for determining the physical condition status of the operator (hereinafter, referred to as "determination reference value") from the registered biological information of the operator (ST901). For example, for the determination reference value, it is preferable to set a reference value that can divide the physical condition status into a plurality of stages (for example, five stages S, and A to D illustrated in FIG. 7). The determination of the physical condition of the operator based on the physical condition may be performed by using artificial intelligence (AI) or the like from a plurality of conditions including the biological information.

As such, the biological information (physical condition management data) of the operator is measured in a state where the determination reference value of the physical condition status is set in the management server 8. The measurement of the biological information is common to the flow illustrated in FIG. 8. In other words, in a state where the determination reference value of the physical condition is set, the measurement start instruction of the biological information is determined (ST801), and when the measurement time comes (ST802), the biological information is acquired (ST803), and the acquired biological information and the like are output to the management server 8 (ST804) and recorded in the management server 8 (ST805).

When the biological information and the like output from the wearable terminal 10 are recorded, the table management unit 86 of the management server 8 determines the physical condition status of the operator from the biological information and records the determined physical condition status in the physical condition management information table 700 (ST902). Accordingly, the physical condition status of the operator is registered in the physical condition management information table 700 in association with the biological information of the operator and the measurement time.

After outputting the biological information and the measurement time, the control unit 11 of the wearable terminal 10 determines whether there is a measurement end instruction of the biological information of the operator (ST903). For example, the control unit 11 determines whether the measurement end instruction is received from the operator via the input unit 14. In a case where the measurement end instruction of the biological information is not detected (ST903: No), the control unit 11 returns the process to ST802 and repeats the processes after ST802. When the measurement end instruction of the biological information is detected while repeating the processes from ST802 to ST804 and ST903 (ST903: Yes), the control unit 11 ends the registration process of a series of biological information (physical condition management information) illustrated in FIG. 9.

Based on the process illustrated in FIG. 9, in the sewing management system 1, after the measurement start of the biological information is instructed, the biological information is continuously measured until the measurement end is instructed, and the biological information and the like are registered in the physical condition management information table 700. Although a case where the biological information is registered as the physical condition management information is described here, it is possible to detect the number of steps of the operator as the activity amount information or count the working hours and the number of breaks of the operator. By registering the pieces of information, for example, the physical condition management information illustrated in FIG. 7 is registered in the physical condition management information table 700.

Figure 10:
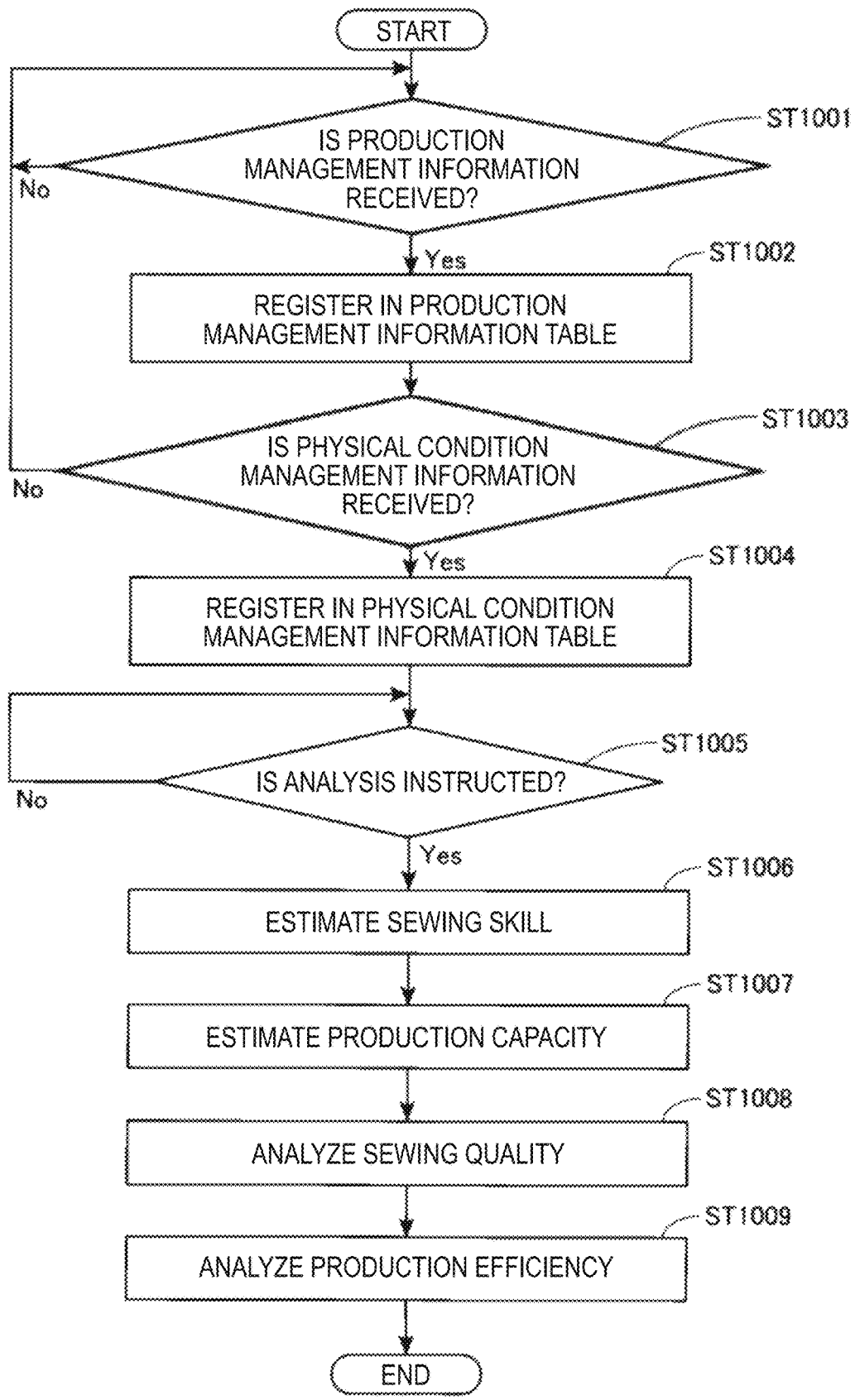
FIG. 10 is a flowchart for describing an analysis process in the management server.

In the sewing management system 1 according to the embodiment, the management server 8 estimates the sewing skill of the operator based on the production management information registered in the production management information table 600, and estimates the production capacity of the operator based on the physical condition management information registered in the physical condition management information table 700. The sewing quality and the production efficiency in the sewing line SL are analyzed according to these estimation results. Hereinafter, an analysis process in the management server 8 will be described with reference to FIG. 10. FIG. 10 is a flowchart for describing the analysis process in the management server 8 according to the embodiment.

As illustrated in FIG. 10, in the management server 8, the control unit 81 constantly monitors whether the production management information is received from the equipment of various processes of the sewing management system 1 (ST1001). In a case where the production management information is not received from the equipment of the various processes (ST1001: No), the control unit 81 continues the monitoring operation. The contents of the production management information determined in ST1001 is preset in the management server 8 by the administrator of the sewing management system 1.

Meanwhile, when the production management information is received from the equipment of various processes (ST1001: Yes), the table management unit 86 registers the production management information in the production management information table 600 (ST1002). The production management information is recorded in the storage unit 82 via the communication unit 85 under the control of the control unit 81. Here, the table management unit 86 registers the production management information stored in the storage unit 82 in various items of the production management information table 600 based on the item number ID.

After registering the production management information in the production management information table 600, the control unit 81 monitors whether the physical condition management information of the operator is received from the wearable terminal 10 of various processes of the sewing management system 1 (ST1003). In a case where the physical condition management information is not received from the wearable terminal 10 (ST1003: No), the control unit 81 returns the process to ST1001 and repeats the processes after ST1001.

Meanwhile, when the physical condition management information is received from the wearable terminal 10 (ST1003: Yes), the table management unit 86 registers the physical condition management information in the physical condition management information table 700 (ST1004). The physical condition management information is recorded in the storage unit 82 via the communication unit 85 under the control of the control unit 81. Here, the table management unit 86 registers the physical condition management information stored in the storage unit 82 in various items of the physical condition management information table 700 based on the operator ID.

Here, a case where the physical condition management information is received and registered in the physical condition management information table 700 (ST1003, ST1004) after the production management information is received and registered in the production management information table 600 (ST1001, ST1002), will be described. However, the order of receiving process and registration process of the pieces of management information may be reversed, or the processes may be performed in parallel.

In the process of registering the production management information and the physical condition management information, the control unit 81 determines whether the analysis instruction is received of the sewing quality and the production efficiency in the sewing line SL from the manager via the input unit 84 (ST1005). In a case where the analysis instruction of the sewing quality and the production efficiency is not received (ST1005: No), the control unit 81 continues the determination operation. While the determination operation is continued, the production management information and the physical condition management information are further registered in the production management information table 600 and the physical condition management information table 700.

In a case where the analysis instruction of the sewing quality and the production efficiency is received (ST1005: Yes), the control unit 81 estimates the sewing skill of the operator based on the production management information registered in the production management information table 600 (ST1006). The sewing skill is estimated by comprehensively considering that the operator can use various sewing machines and can handle various processes, but here, the estimation of the sewing skill of one process will be described. The sewing skill estimated in ST1006 indicates how much a product satisfying a predetermined reference can be sewn within a predetermined time.

Here, a case where the sewing skill of the operator is estimated by taking the production management information of the numbers #1 to #3 registered in the production management information table 600 as an example will be considered. Here, while the control unit 81 estimates that the sewing skills of the operators OP1 and OP2 are equal to or higher than a certain level, the control unit 81 estimates that the sewing skill of the operator OP3 is below a certain level, based on the contents of the production management information illustrated in FIG. 6.

For example, the control unit 81 can estimate the sewing skill of the operator from the contents of the operation data 1 and 2 (more specifically, the contents of the operation data 1 and 2 compared to the standard parameters 1 and 2) registered in the production management information table 600. Here, while OP1 and OP2 are working with the contents (TS3, NS3) of the operation data 1 and 2 with respect to the contents (TS2, NS2) of the standard parameters 1 and 2, OP3 is working with the contents (TS1, NS1) of the operation data 1 and 2 with respect to the contents (TS2, NS2) of the standard parameters 1 and 2. Therefore, while the sewing skills of the operators OP1 and OP2 are equal to or higher than a certain level, the control unit 81 estimates that the sewing skill of the operator OP3 is below a certain level.

The control unit 81 can estimate the sewing skill of the operator from the inspection result of the product of the operator which is registered in the production management information table 600. Here, while the inspection result of the products of the operators OP1 and OP2 is the number of defects "0", the inspection result of the product of the operator OP3 is the number of defects "3". Therefore, while the sewing skills of the operators OP1 and OP2 are equal to or higher than a certain level, the control unit 81 estimates that the sewing skill of the operator OP3 is below a certain level. It can be said that the sewing skill of the operator estimated based on the inspection result of the product represents the quality of the product sewn by the operator (sewing quality).

The control unit 81 can estimate the sewing skill of the operator from the volume data registered in the production management information table 600. Here, the volume data of the products of the operators OP1, OP2, and OP3 are 100, 80, and 60, respectively. Therefore, the control unit 81 estimates that the sewing skill of the operator decreases in the order of OP1, OP2, and OP3. It can be said that the sewing skill of the operator estimated based on the volume data of the product represents the work efficiency of the operator.

When estimating the sewing skill of the operator as described above, it is preferable that the control unit 81 considers the defect data of the sewing machine 9 specified by the sewing machine ID (the number of occurrences of defects that have occurred in the sewing machine 9). For example, by considering the influence of the defect data of the sewing machine 9 on the volume data and the inspection result data, it is possible to accurately estimate the original sewing skill of the operator.

In the above description, for convenience of description, it is described whether the sewing skill of the operator is equal to or higher than a certain level or below a certain level. In other words, a case where the sewing skill of the operator is estimated in two stages is illustrated. However, the estimation reference of the sewing skill of the operator is not limited thereto. In order to accurately estimate the sewing skill of the operator, it is preferable as an embodiment to quantify the sewing skill based on a predetermined multi-stage reference. Here, the sewing skill of the operator is quantified by comprehensively determining the contents of various pieces of production management information included in the production management information table 600.

For example, it is considered to add or deduct points according to the contents of each item using the value of the volume data in the production management information as a reference. For example, while points are added (for example, 5 points are added) respectively in a case where the sewing time and the sewing speed of the standard parameters 1 and 2 are increased, points are deducted (for example, 5 points are deducted) in a case where the sewing time and the sewing speed are decreased. The points are added or deducted according to the number of defects in the inspection result data. The value of the defect data is added by the value.

In a case of adding or subtracting the points as such, the sewing skills of the operators OP1, OP2, and OP3 are required as follows.

(Sewing Skill of Operator OP1)

100 (volume data)+10 (change of setting parameters 1 and 2)+0 (inspection result data)+0 (defect data)=100

(Sewing Skill of Operator OP2)

80 (volume data)+10 (change of setting parameters 1 and 2)+0 (inspection result data)+0 (defect data)=80

(Sewing Skill of Operator OP3)

60 (volume data)−10 (change of setting parameters 1 and 2)−3 (inspection result data)+10 (defect data)=57

Figures 11, 12:
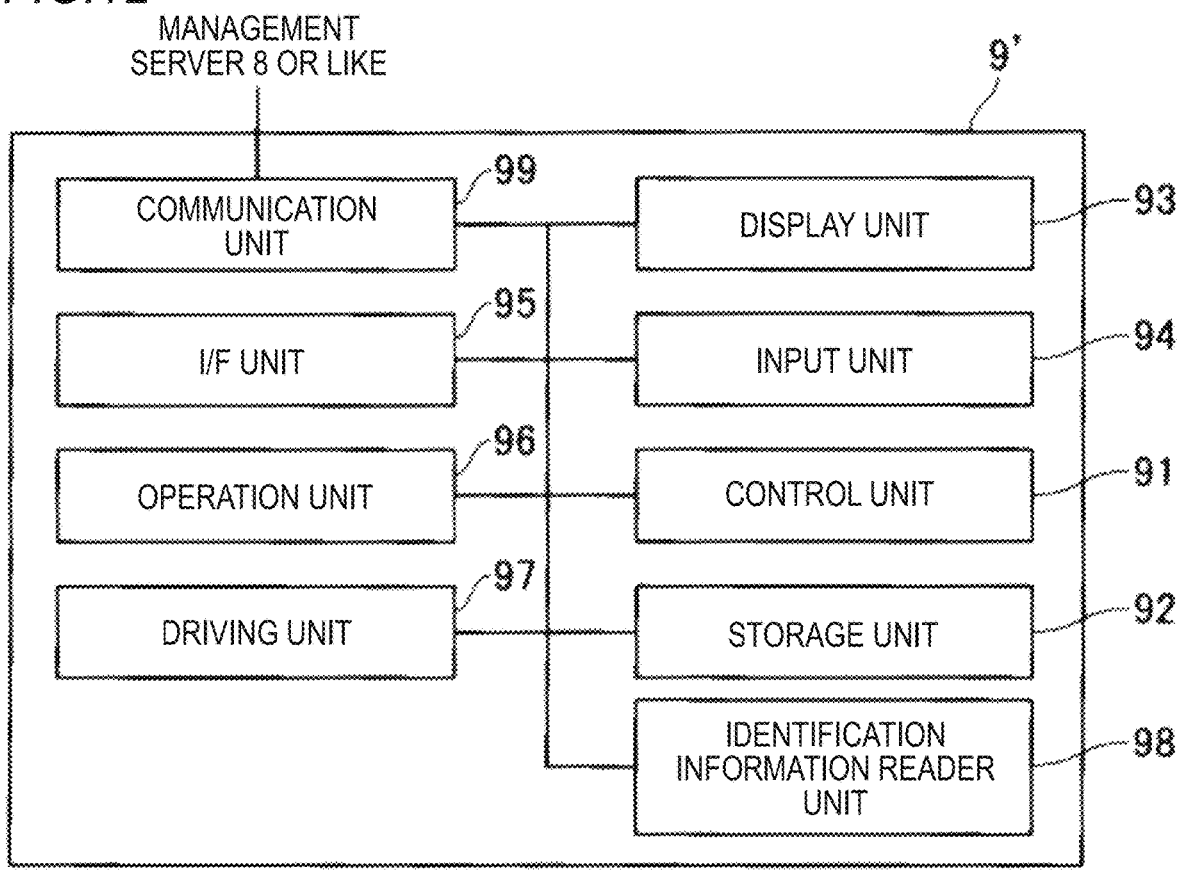
FIG. 11 is an explanatory view of an example of a sewing skill table held in the table holding unit of the management server.
FIG. 12 is a block diagram illustrating a configuration of the sewing machine included in the sewing management system according to a modification example of the present embodiment.

Therefore, here, it is estimated that the sewing skill of OP1 is the highest, followed by the sewing skills of OP2 and OP3. The sewing skill estimated as such is registered in a sewing skill table 1100 (refer to FIG. 11). As illustrated in FIG. 11, in the sewing skill table 1100, the sewing skills (more specifically, values corresponding to the sewing skills) are registered in association with the operator ID and the process ID.

After estimating the sewing skill of the operator, the control unit 81 estimates the production capacity of the operator from the estimated sewing skill of the operator and the current physical condition status of the operator registered in the physical condition management information table 700 (ST1007). The production capacity of the operator can be estimated by, for example, multiplying the above-described numerical value indicating the sewing skill of the operator (hereinafter, appropriately referred to as "sewing skill value") by a coefficient that corresponds to the physical condition status (hereinafter, appropriately referred to as "status coefficient").

For example, the status coefficient is set to "1.2" in a case where the physical condition status is "S", set to "1.0" in a case where the physical condition status is "A", set to "0.8" in a case where the physical condition status is "B", set to "0.6" in a case where the physical condition status is "C", and set to "0.4" in a case where the physical condition status is "D". By multiplying the sewing skill value by the status coefficient as such, the production capacity can be accurately estimated according to the physical condition of the operator.

After estimating the production capacity of the operator OP, the control unit 81 analyzes the sewing quality of the sewing line SL (ST1008). For example, the control unit 81 comprehensively determines the sewing skill of the operator estimated in ST1006 and analyzes the sewing quality of the sewing line SL. For example, the control unit 81 can analyze the sewing quality of the sewing line SL by considering the above-described sewing skill value of the operator assigned to the sewing line SL. While the control unit 81 analyzes that the sewing quality is high in the sewing line SL when the sewing skill value of the operator is equal to or higher than a predetermined value, the control unit 81 can analyze that the sewing quality in the sewing line SL is low when the sewing skill value is below the predetermined value.

When analyzing the sewing quality of the sewing line SL, it is preferable as an embodiment to multiply production management information by the coefficient that directly increases the value (for example, the value of the inspection result data) of the item representing the sewing quality. Here, it becomes possible to more accurately analyze the sewing quality in the sewing line SL.

After analyzing the sewing quality in the sewing line SL, the control unit 81 analyzes the production efficiency of the sewing line SL (ST1009). For example, the control unit 81 comprehensively determines the production capacity of the operator estimated in ST1007 and analyzes the work efficiency of the sewing line SL. For example, the control unit 81 can analyze the work efficiency of the sewing line SL by adding a value (production capacity value) indicating the production capacity of the operator assigned to the sewing line SL. While the control unit 81 analyzes that the work efficiency is high in the sewing line SL when the production capacity value of the operator is equal to or higher than a predetermined value, the control unit 81 can analyze that the work efficiency in the sewing line SL is low when the production capacity value is below the predetermined value.

When analyzing the work efficiency of the sewing line SL, it is preferable as an embodiment to multiply production management information by the coefficient that directly increases the value (for example, the value of the volume data) of the item representing the work efficiency. Here, it becomes possible to more accurately analyze the work efficiency in the sewing line SL.

By displaying such an analysis result on the display unit 83, the manager of the management server 8 can confirm the analysis result of the sewing quality and the production efficiency in the sewing line SL. A location where the sewing quality and the production efficiency in the sewing line SL are low can be specified according to these estimation results. Accordingly, the manager can take measures for improving the sewing quality and the production efficiency, such as reassignment of operators and training of sewing skills.

When displaying the analysis result on the display unit 83, it is preferable as an embodiment to change the color scheme of the icon of the operator based on the physical condition statuses of the operators assigned to each process of the sewing line SL. For example, in a case where the physical condition status is "S", the icon is green, and in a case where the physical condition status is "A", "B", "C", and "D", the icon can be respectively blue, yellow, pink, and red. By changing the color scheme of the icon of the operator as such, the physical condition of the operator can be intuitively grasped, and the situation of production efficiency in the sewing line SL can also be grasped.

As such, in the sewing management system 1 according to the embodiment, the production management information including the operator ID and the operation information of the sewing machine 9 is managed for each process of producing the product sewn in the sewing line SL, and the physical condition management information is managed for each operator. The sewing skill of the operator is estimated based on the production management information, and the production capacity of the operator is estimated based on the physical condition management information. Accordingly, by setting the personnel assignment and the like in the sewing line SL, it is possible to improve the sewing quality and the production efficiency in the sewing line SL.

The timing for setting the personnel assignment and the like in the sewing line SL may be the timing when the production capacity of the operator is reduced. The personnel assignment may be set based on the tendency that can be determined from the accumulated data. The personnel assignment may be set before the production capacity deteriorates in advance based on the sign of the deterioration in the production capacity of the operator using artificial intelligence (AI) or the like from the accumulated data.

In particular, in the sewing management system 1, the management server 8 determines the physical condition status of the operator based on the physical condition management information, and estimates the production capacity of the operator by adjusting the sewing skill of the operator with the physical condition status. Accordingly, the production capacity of the operator is estimated by adjusting the sewing skill with the physical condition status determined based on the physical condition management information. Accordingly, the production capacity can be accurately estimated according to the physical condition of the operator.

In the sewing management system 1, the wearable terminal 10 detects the biological information of the operator as an example of the physical condition management information. The management server 8 determines the physical condition status of the operator according to the biological information detected by the wearable terminal 10. Accordingly, it is possible to accurately determine the physical condition status according to the biological information of the operator.

In the sewing management system 1, the wearable terminal 10 detects the activity amount information of the operator as an example of the physical condition management information. The management server 8 determines the physical condition status of the operator according to the activity amount information detected by the wearable terminal 10. Accordingly, it is possible to accurately determine the physical condition status according to the activity amount information of the operator.

According to the sewing management system 1, it is possible to improve the sewing quality and the production efficiency in the sewing line SL, and additionally, it is also possible to improve the management efficiency of labor management of operators who work in the sewing line SL. In the production management information table 600 illustrated in FIG. 6, the contents related to the degree of business contribution by the operator are registered. In particular, the production capacity of the operator obtained in ST1007 of FIG. 10 is a content directly related to the degree of business contribution. It is preferable as an embodiment to determine the treatment such as salary of the operator and the necessity of taking a vacation based on the pieces of information.

The technology of the disclosure is not limited to the above-described embodiment and the modification example, and various modifications, substitutions, and changes may be made without departing from the spirit of the technical idea. When the technical idea can be realized in another manner by the advancement of technology or another derivative technology, the disclosure may be realized using the method. Therefore, the range of the claims cover all embodiments that may be included within the scope of the technical idea.

For example, in the above-described embodiment, a case where the operator ID and the item number ID are read by the mobile terminal 40 connected to the sewing machine 9 are described. However, the configuration for reading the operator ID and the item number ID is not limited thereto, and can be changed as appropriate. For example, the sewing machine 9 may have a configuration for reading the operator ID and the item number ID. In the above-described embodiment, the mobile terminal 40 is provided with the communication unit 47 for communicating with the management server 8 and the like via the network NW2 of the sewing management system 1, but the sewing machine 9 may be provided with the communication unit. In the above-described embodiment, a configuration in which the mobile terminals 30, 50, 60, and 70 are provided in the various processes that configure the sewing line SL is employed, but in a case where the equipment used in various processes such as a cutting machine, an iron press machine, and an inspection machine has a communication function for communicating with the management server 8 or the like via the network, a configuration in which the mobile terminal is not provided may also be employed.

In the above-described embodiment, a case where the production management information is managed for each process of the component that configures the product according to the item number ID in the production management information table, is described. However, the management method of the production management information is not limited thereto, and can be changed as appropriate. For example, the production management information may be managed for each process of the product according to the item number ID associated with the product.

In the above-described embodiment, a case where the management server 8 is connected to the network NW2 of the sewing line SL of the sewing factory SP1 is described. However, the configuration of the management server 8 is not limited thereto, and can be changed as appropriate. For example, the management server 8 may be connected to the network NW1 that connects a plurality of sewing factories to each other. The function of the management server 8 may be provided on the cloud. The management server 8 is not limited to a case where the sewing line SL is independently configured, and for example, the PC assigned to the execution region of the specification generation process 2 may have the function.

In the above-described embodiment, a case where the terminal 10 for detecting the physical condition management information of the operator is configured with the wearable terminal 10 is described. A case of detecting the body temperature, heart rate, blood pressure, and the like of the operator as the biological information detected by the wearable terminal 10 will be described. As the biological information detected by the terminal 10 (wearable terminal 10), brain waves may be detected. By detecting the brain waves, for example, the mental state of the operator can be determined. Accordingly, it is possible to determine the anxiety or excitement felt by the operator. As a result, the physical condition of the operator including the mental state can be determined, and the production capacity of the operator can be estimated more accurately.

In the above-described embodiment, a case where the operator ID is read as the identification information from the ID card carried by the operator is described, but the operator may be specified by the face authentication or fingerprint authentication of the operator.

In the above-described embodiment, a case where the identification information is read by the identification information reader unit 46 of the mobile terminal 40 is described, but the reading of the identification information is not limited to the mobile terminal 40 and may be performed by the sewing machine 9. FIG. 12 is a block diagram illustrating a configuration of a sewing machine 9 included in the sewing management system according to a modification example of the embodiment. In FIG. 12, the same reference numerals will be given to the configurations common to those in FIG. 2. As illustrated in FIG. 12, in addition to the configuration illustrated in FIG. 2, the sewing machine 9 includes an identification information reader unit 98 and a communication unit 99. The identification information reader unit 98 reads the operator ID in the ID card carried by the operator, the item number ID in the RFID tag attached to the cloth, or the like in a non-contact manner. The communication unit 99 communicates with the management server 8 and the like via the network NW2 of the sewing management system 1. Even in a case where the configuration of the sewing machine is changed as such, the same effect as that of the above-described embodiment can be obtained.

The feature points in the above-described embodiments are summarized below.

According to the above-described embodiment, there is provided a sewing management system including: a sewing device that transmits production management information including identification information of an operator and operation information of a device main body; a terminal that detects physical condition management information of the operator; and a management device that manages the production management information for each process of a product sewn in a sewing line or for each process of a component that configures the product, and manages the physical condition management information for each operator, in which the management device estimates a sewing skill of the operator based on the production management information and estimates production capacity of the operator based on the physical condition management information. Accordingly, the production management information including the identification information of the operator and the operation information of the sewing device is managed for each process of a product sewn in a sewing line or for each process of a component that configures the product, and the physical condition management information is managed for each operator. The sewing skill of the operator is estimated based on the production management information, and the production capacity of the operator is estimated based on the physical condition management information. Accordingly, by setting the personnel assignment and the like in the sewing line, it is possible to improve the sewing quality and the production efficiency in the sewing line.

In the sewing management system according to the above-described embodiment, the management device determines a physical condition status of the operator based on the physical condition management information, and estimates the production capacity of the operator by adjusting the sewing skill of the operator with the physical condition status. Accordingly, the production capacity of the operator is estimated by adjusting the sewing skill with the physical condition status determined based on the physical condition management information. Accordingly, the production capacity can be accurately estimated according to the physical condition of the operator.

In the sewing management system according to the above-described embodiment, the terminal detects biological information of the operator as the physical condition management information, and the management device determines the physical condition status of the operator according to the biological information. Accordingly, the physical condition status is determined according to the biological information of the operator detected by the terminal. Accordingly, it is possible to accurately determine the physical condition status according to the biological information of the operator.

In the sewing management system according to the above-described embodiment, the terminal detects activity amount information of the operator as the physical condition management information, and the management device determines the physical condition status of the operator according to the activity amount information. Accordingly, the physical condition status is determined according to the activity amount information of the operator detected by the terminal. Accordingly, it is possible to accurately determine the physical condition status according to the activity amount information of the operator.

In the sewing management system according to the above-described embodiment, the terminal is configured with a wearable terminal detachably attached to the body of the operator. Accordingly, since the terminal is configured with the wearable terminal, the biological information and the activity amount information of the operator can be detected without interfering with the work in the sewing line SL.

According to the above-described embodiment, there is provided a sewing management method using a sewing device that performs sewing in a sewing line, a management device that manages each piece of information in the sewing line, and a terminal that detects physical condition management information of an operator of the sewing line, the method including: a step of transmitting production management information including identification information of the operator and operation information of the sewing device, from the sewing device; a step of transmitting the physical condition management information of the operator from the terminal; a step of managing the production management information for each process of a product sewn in the sewing line or for each process of a component that configures the product, by the management device; a step of managing the physical condition management information for each operator, by the management device; a step of estimating a sewing skill of the operator based on the production management information, by the management device; and a step of estimating production capacity of the operator based on the sewing skill and the physical condition management information of the operator, by the management device. Accordingly, the production management information including the identification information of the operator and the operation information of the sewing device is managed for each process of a product sewn in a sewing line or for each process of a component that configures the product. The physical condition management information is managed for each operator. The sewing skill of the operator is estimated based on the production management information, and the production capacity of the operator is estimated based on the physical condition management information. Accordingly, by setting the personnel assignment and the like in the sewing line, it is possible to improve and maintain the sewing quality and the production efficiency in the sewing line.

What is claimed is:

1. A sewing management system comprising:
   a sewing device that transmits production management information including identification information of an operator and operation information of a device main body;
   a terminal that detects physical condition management information of the operator; and
   a management device that manages the production management information for each process of a product sewn in a sewing line or for each process of a component that configures the product, and manages the physical condition management information for each operator, wherein
   the management device estimates a sewing skill of the operator based on the production management information and estimates production capacity of the operator based on the physical condition management information.

2. The sewing management system according to claim 1, wherein
   the management device determines a physical condition status of the operator based on the physical condition management information, and estimates the production capacity of the operator by adjusting the sewing skill of the operator with the physical condition status.

3. The sewing management system according to claim 2, wherein
   the management device estimates the production capacity of the sewing line based on the production capacity of the operator.

4. The sewing management system according to claim 3, wherein
   the management device sets personnel assignment of the sewing line based on the estimated production capacity of the operator.

5. The sewing management system according to claim 1, wherein
   the terminal detects biological information of the operator as the physical condition management information, and
   the management device determines the physical condition status of the operator according to the biological information.

6. The sewing management system according to claim 1, wherein
   the terminal detects activity amount information of the operator as the physical condition management information, and
   the management device determines the physical condition status of the operator according to the activity amount information.

7. The sewing management system according to claim 1, wherein
   the terminal is a wearable terminal configured to be detachably attached to a body of the operator.

8. A sewing management method using a sewing device that performs sewing in a sewing line, a management device that manages each piece of information in the sewing line, and a terminal that detects physical condition management information of an operator of the sewing line, the method comprising:
   a step of transmitting production management information including identification information of the operator and operation information of the sewing device, from the sewing device;
   a step of transmitting the physical condition management information of the operator from the terminal;
   a step of managing the production management information for each process of a product sewn in the sewing line or for each process of a component that configures the product, by the management device;
   a step of managing the physical condition management information for each operator, by the management device;
   a step of estimating a sewing skill of the operator based on the production management information, by the management device; and
   a step of estimating production capacity of the operator based on the sewing skill and the physical condition management information of the operator, by the management device.

9. The sewing management method according to claim 8, further comprising:
   a step of estimating production capacity of the sewing line based on the production capacity of the operator, which is estimated by the management device.

10. The sewing management method according to claim 8, further comprising:
    a step of setting personnel assignment of the sewing line based on the production capacity of the operator, which is estimated by the management device.

* * * * *